(12) United States Patent
Hockaday et al.

(10) Patent No.: US 6,772,448 B1
(45) Date of Patent: Aug. 10, 2004

(54) NON-FOGGING GOGGLES

(75) Inventors: Robert G. Hockaday, Los Alamos, NM (US); Patrick S. Turner, Los Alamos, NM (US); Zachary Bradford, Los Alamos, NM (US); Marc D. DeJohn, Los Alamos, NM (US); Carlos J. Navas, Santa Fe, NM (US); Heathcliff L. Vaz, Los Alamos, NM (US)

(73) Assignee: Energy Related Devices, Inc., Los Alamos, NM (US)

( * ) Notice: Subject to any disclaimer, the term of this patent is extended or adjusted under 35 U.S.C. 154(b) by 0 days.

(21) Appl. No.: 10/317,065

(22) Filed: Dec. 12, 2002

Related U.S. Application Data

(60) Provisional application No. 60/339,394, filed on Dec. 14, 2001.

(51) Int. Cl.[7] .................................................. A61F 9/02
(52) U.S. Cl. ............................................... 2/435; 2/436
(58) Field of Search ........................... 2/426, 435, 436, 2/437, 439, 440, 445; 351/41, 43

(56) References Cited

U.S. PATENT DOCUMENTS

| | | | |
|---|---|---|---|
| 2,612,639 A | | 10/1952 | Christensen et al. |
| 2,612,640 A | * | 10/1952 | Palmes .......................... 2/436 |
| 2,615,162 A | | 10/1952 | Christensen et al. |
| 2,617,099 A | * | 11/1952 | Christensen et al. ........... 2/435 |
| 2,618,782 A | | 11/1952 | Christensen et al. |
| 2,619,642 A | * | 12/1952 | Christensen et al. ........... 2/436 |
| 2,619,643 A | | 12/1952 | Christensen et al. |
| 3,591,864 A | | 7/1971 | Allsop |
| 3,718,937 A | * | 3/1973 | Smith ............................ 2/436 |
| 4,150,443 A | * | 4/1979 | McNeilly ....................... 2/436 |
| 4,290,673 A | | 9/1981 | Yamamoto |
| 4,317,240 A | | 3/1982 | Angerman et al. |
| 4,435,852 A | * | 3/1984 | Nesler ........................... 2/436 |
| 4,443,893 A | * | 4/1984 | Yamamoto ..................... 2/436 |
| 4,447,914 A | | 5/1984 | Jannard |
| 4,584,721 A | | 4/1986 | Yamamoto |
| 4,707,863 A | | 11/1987 | McNeal |
| 5,018,223 A | | 5/1991 | Dawson et al. |
| 5,363,512 A | | 11/1994 | Grabos, Jr. et al. |
| 5,452,480 A | | 9/1995 | Ryden |
| 5,542,130 A | | 8/1996 | Grabos, Jr. et al. |
| 5,617,588 A | * | 4/1997 | Canavan et al. ............... 2/428 |
| 5,652,965 A | | 8/1997 | Crooks |
| 5,689,834 A | | 11/1997 | Wilson |
| 5,966,746 A | * | 10/1999 | Reedy et al. ................... 2/436 |
| 6,049,917 A | | 4/2000 | Hyden |
| 6,152,137 A | * | 11/2000 | Schwartz et al. ........... 128/846 |

* cited by examiner

*Primary Examiner*—Gary L. Welch
(74) *Attorney, Agent, or Firm*—James Creighton Wray; Meera P. Narasimhan

(57) ABSTRACT

A goggle resistant to fogging is provided. The goggle consists of a water wicking and thermal transfer face gasket combined with heat transfer inlets and outlets optimized for heat transfer to air flow through the goggle. With low airflow resistance in the vertically oriented inlets and outlets, the goggle ventilates by natural convection removing moisture and keeping the goggle from fogging. Simultaneously, the present goggle results in greater comfort for the user.

64 Claims, 10 Drawing Sheets

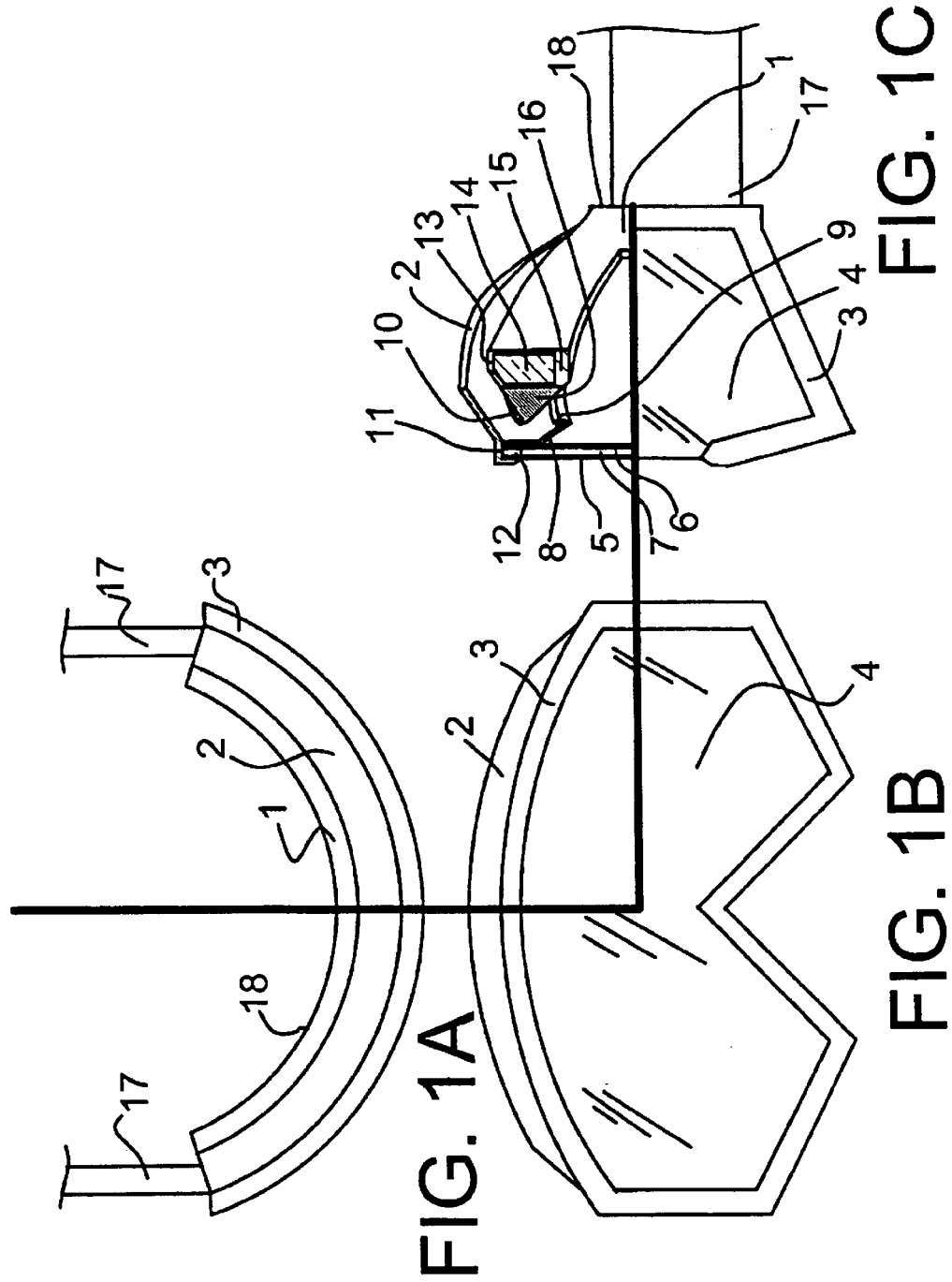

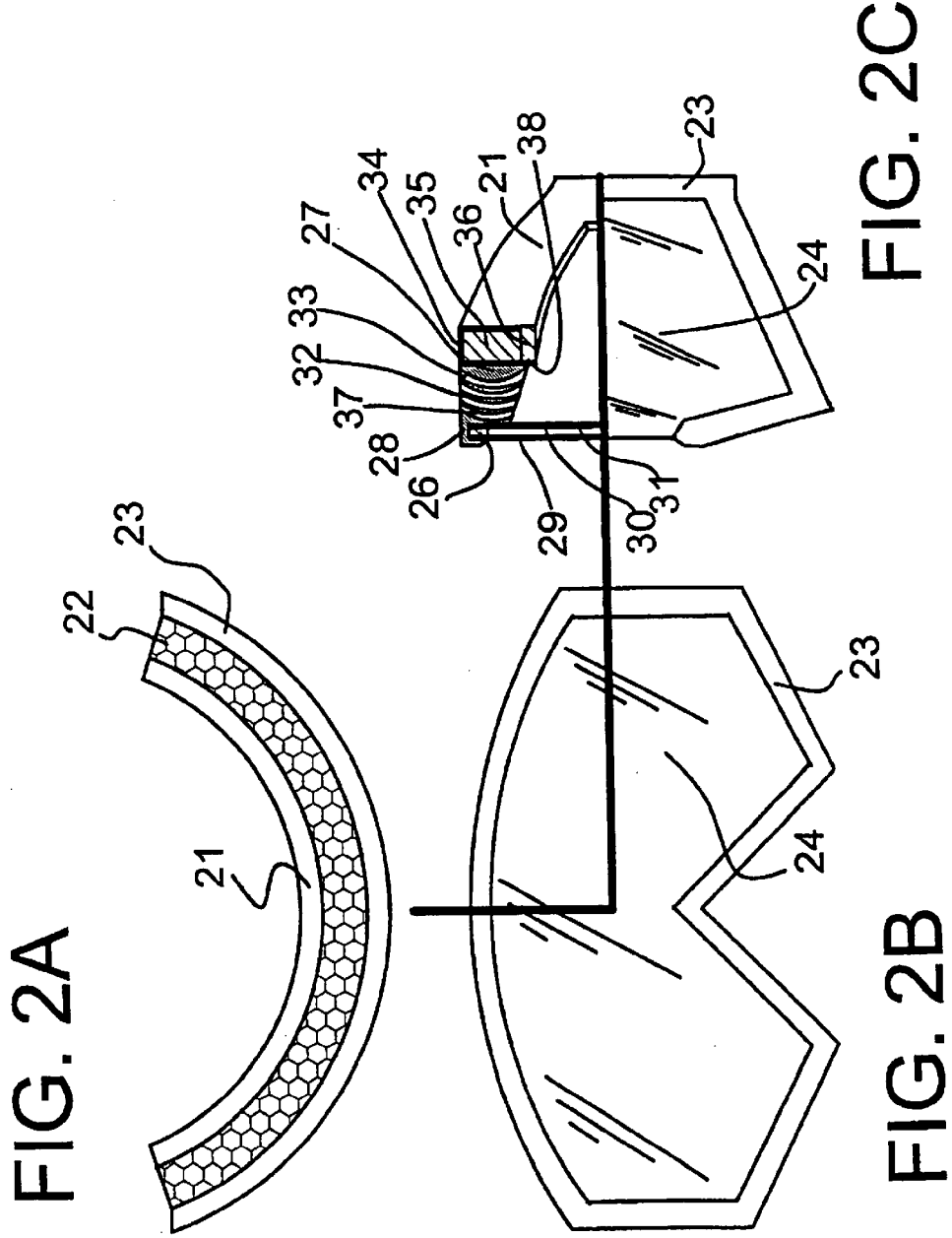

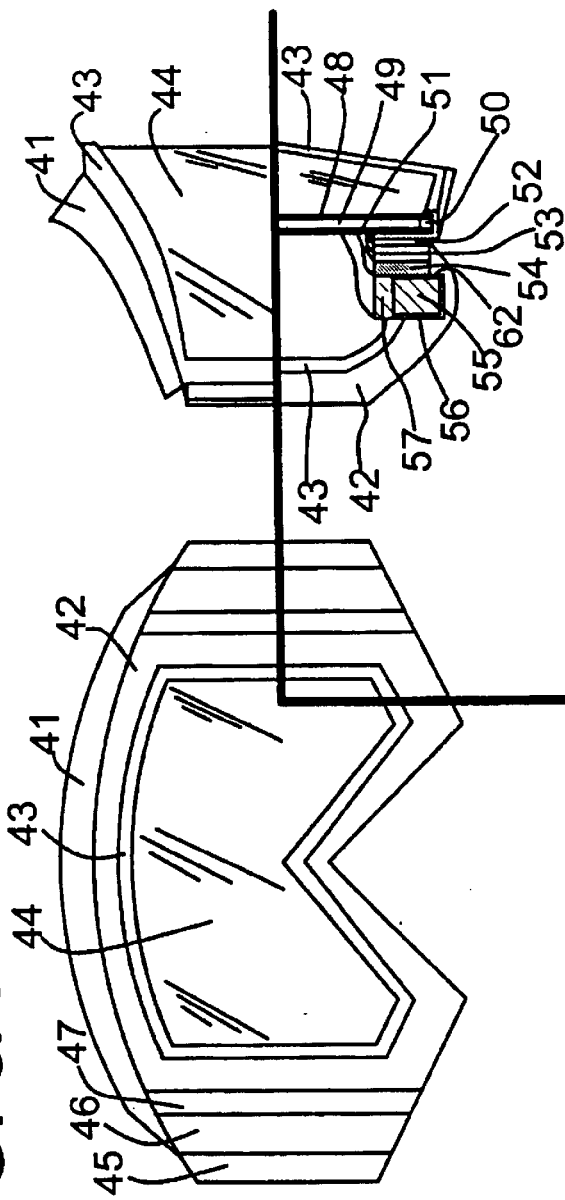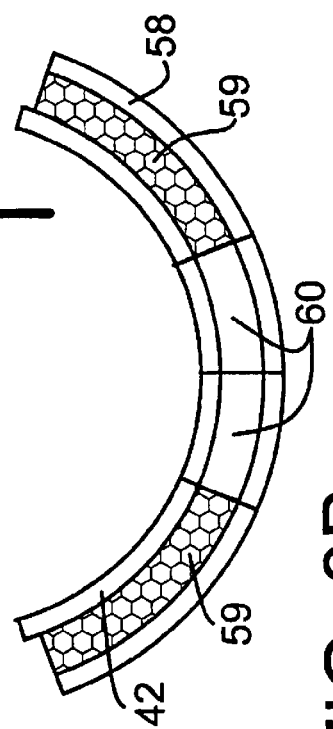

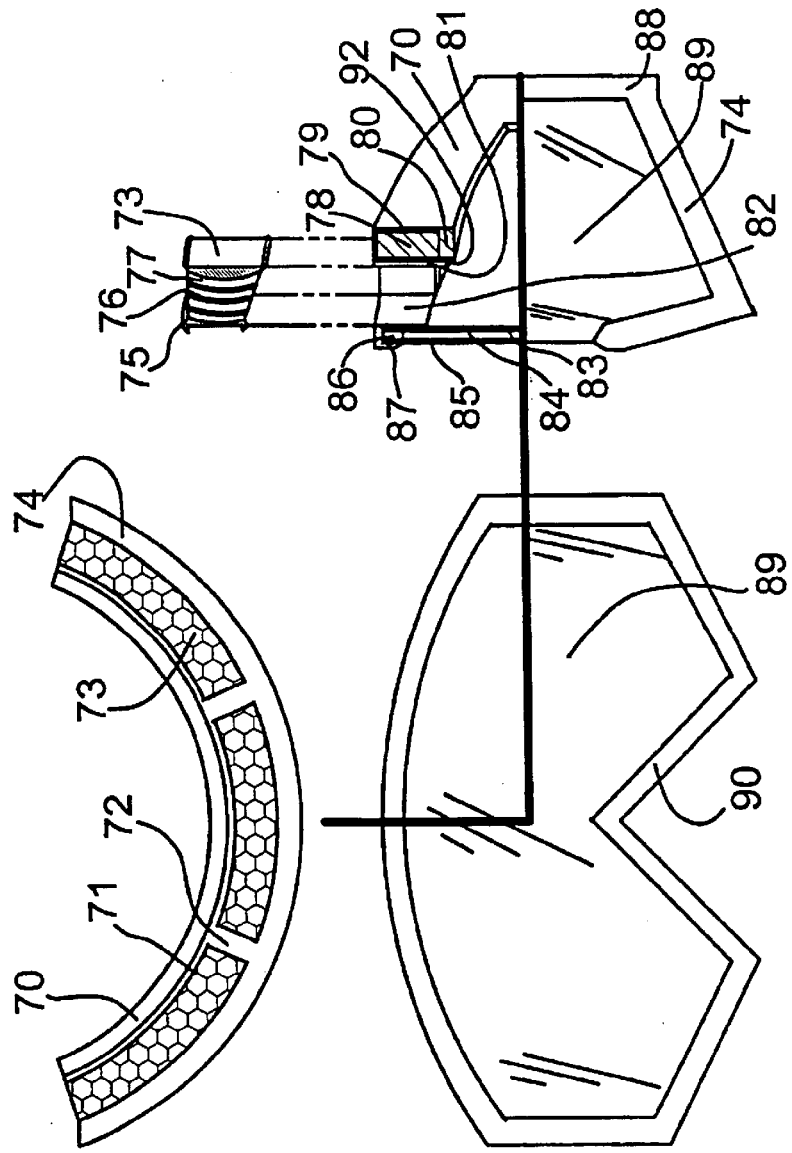

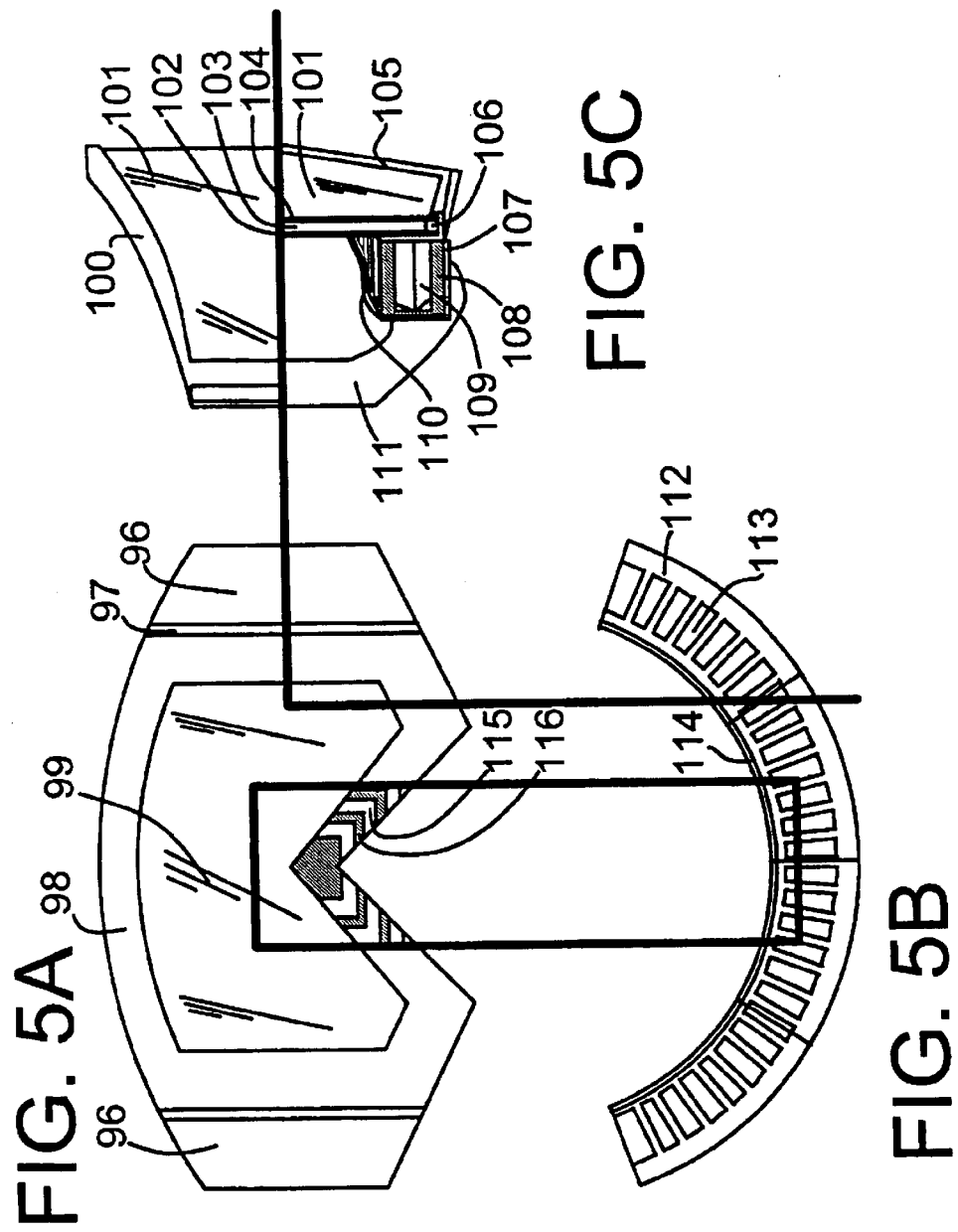

NON-FOGGING GOGGLES

This application claims the benefit of U.S. Provisional Application No. 60/339,394, filed Dec. 14, 2001.

BACKGROUND OF THE INVENTION

The problem of fogging of sports goggles has been known for many years. In ski goggles this effect takes place when the temperature on the interior of the lens reaches the dew point from the combination of cooling of the lens in contact with the cold air outside, and the flux of moisture from the face into the interior air volume. The fundamental concept to reduce fogging in goggles is to achieve an air temperature in the goggle above the dew point at the surface of the inner lens. The counter actions are to add heat and remove moisture from the interior of the goggle. Attempts at making non-fogging goggles are quite numerous and typically rely on a variety of different techniques.

The following are some examples:

Electric heating of the lens.

Increasing the thermal insulation capability of the lenses by using two lenses with an air gap between them. This reduces the heat flow through the lens and subsequently allows the inner lens surface temperature to come closer to that of the skin surface, thus raising the inner lens temperature above the dew point in the goggle.

Increasing the radiant heat trapping of the goggle lens by coating the surfaces of the lenses facing each other and the outer surface with infrared reflective and low emissivity films. This reduces the lens radiation heat transfer losses. Again this technique subsequently allows the lens surface temperature to be closer to that of the skin surface, thus raising the temperature of the inner lens surface above the dew point in the goggle.

Increasing the radiant heat transfer from the skin to the inner lens, by choosing or coating the inner lens with an infrared absorbing layer on the inner-facing surface of the inner lens. This maximizes the radiant heat transfer from the face to the inner lens, thus allowing the inner lens surface temperature to be closer to that of the skin surface, and raising the temperature of the lens above the dew point in the goggle.

Increasing the air gap between the inner and outer lens. This further decreases the heat loss through the lens and subsequently allows the lens surface temperature to be closer to that of the skin surface, thus raising inner lens surface temperature above the dew point in the goggle.

All three of the thermal insulation techniques mentioned above alone does not result in defogging the goggle because the air just above the surface of the skin and eyes is close to 100% relative humidity and the insulation is not perfect. Thus, the lens is colder than the skin surface and condensation will occur as water diffuses from the skin surface to the lens. Therefore using a thermally resistant lens needs to be coupled to a means of removing the moisture from the skin surface and the volume of air in the interior of the goggle.

The following are several techniques of flowing air into a goggle and transferring heat by airflow:

Use metal foils inside the goggle to transfer heat from the top of the goggle, in which the warmer and lighter air rises, to the incoming air in the bottom of the goggle.

Use various vents that draw or force air through the goggle while the skier is moving.

Heat exchange between incoming air and the outgoing air.

Use a fan to draw air through the goggles.

Use adjustable apertures or lift the face pad to increase or decrease air flow.

The following are techniques to condense water or absorb water vapor in the interior of the goggle:

Use metallic conductors to provide condensation areas inside the goggles.

Use thin lens areas of high heat transfer that condense water.

Use chemical absorbents in a liner on the sides of the lenses, or the lenses themselves, to absorb moisture.

In general, the above techniques are either ineffective in achieving a satisfactory non-fogging effect in the full range of ski conditions or are costly and complex in commercial products.

U.S. Pat. No. 2,612,639, Christensen et al.; "Closed Goggles Structure", describes heat exchangers and condensers for circulation of air and dehumidification. They mention using direct air contact with the face to heat the air in the eyecup cavities. They claim a use of high thermal conductivity material in the condensers, but they do not mention using the high thermal conductivity elements to conduct heat from the user to the air.

U.S. Pat. No. 2,615,162, Christensen et al.; "Cold Weather Goggles", describes using condensers and heat exchangers with closed air circulation in a goggle. They do not describe using heat from the user though conductors to heat the air in the eyecup cavities.

U.S. Pat. No. 2,618,782, Christensen et al.; "Goggles Structure", describes forming inlets and outlets of material of high thermal conductivity. Uses the conductivity of the inlets and outlets to dissipate the heat from the top of the goggle to reduce "the absorption of moisture of air in the eye cup cavity". This patent also describes insertable air passage-ways: "Although the above outlet structures are formed of flexible copper or other thin metallic conductor material, it will be apparent that rubber or plastic adaptation of this model can be constructed for insertion with the goggles frame." This patent does not describe using the heat conducted from the body to heat the inlets or outlets.

U.S. Pat. No. 2,619,643, Christensen et al.: "Cold Weather Goggles", describes using metal heat exchanger to condense the moisture and simultaneously dry and heat the incoming air. They do not mention heating the incoming air through the frame to avoid fogging, nor do they describe using heat transfer from the face contact to the air passages.

U.S. Pat. No. 3,591,864, Allsop: "Nonfog Goggles", describes a double lens for goggles, with a flexible woven wire mesh of high thermoconductivity in the frame. The mesh keeps snow out but is loose enough that moisture condenses.

U.S. Pat. No. 4,290,673, Yamamoto; "Ski Goggles", describes double lens goggles with the space between the lenses being heat insulating. Inner lens has an air port at one end close to the frame and a water-repellent air-permeable filter opposed the air port. No references to wicking or heating incoming air.

U.S. Pat. No. 4,317,240, Angerman et al.; "Sports Goggle", describes a single lens goggle with a dual frame design with improved ventilation characteristics.

U.S. Pat. No. 4,584,721, Yamamoto; "Device for Use in Helmet for Preventing Fogging by Electric Heating", describes a transparent electroconductive film in the lens used to generate heat with the passing of electric current.

U.S. Pat. No. 4,370,914, Harris; "Eye Protectors", describes goggles with frames comprising rearwardly angled cowls to improve ventilation characteristics.

U.S. Pat. No. 4,707,863, McNeal; "Anti-Fog Goggle with Foam Frame", describes goggles with foam frame with air channels incorporated to improve ventilation characteristics.

U.S. Pat. No. 5,018,223, Dawson et al.; "Non-Fogging Goggles", describes double lens goggles with a vacuum-deposited metal coating film on the outer lens. Body heat radiated through the metal film serves to lower the temperature differential between the outside and the inside of the goggles.

U.S. Pat. No. 5,452,480, Ryden; "Ski Goggles", describes a fan used to exhaust air from the air space between the goggles and a user's face in order to improve ventilation characteristics.

U.S. Pat. Nos. 5,363,512 and 5,542,130, Grabos, Jr. et al.; "Protective Goggle and Lens with Adjustable Ventilation", describes goggles with adjustable ventilation ports in the frame with a shutter.

U.S. Pat. No. 5,652,965, Crooks; "Non-Fogging Goggles", describes goggles with screened and unrestricted air ports, which control the amount of air passing through the goggles.

U.S. Pat. No. 5,689,834, Wilson; "Goggles", describes heat sinks used in the goggle structure to dissipate heat inside the goggles. Additional air ventilation ports are disclosed.

U.S. Pat. No. 6,049,917, Ryden; "Air Injection Sports Goggle and Method", describes a ventilating fan on the top side of a sport goggle which pulls air in through an air injection hole to improve ventilation characteristics.

SUMMARY OF THE INVENTION

In order to overcome the shortcomings described above, the present invention discloses a device that combines and optimizes several physical functions into components to achieve the desired effect.

We have found in our research that a human will emit between 0.022 mg/sec (resting) and 0.51 mg/sec (strenuous exercise) of water over an approximate facial surface area of 110 cm$^2$. To remove moisture, air from outside the goggle can flow through the goggle, or moisture can diffuse out. If the relative humidity of the outside air is high, raising the temperature of the air is needed for the airflow to carry moisture from the interior of the goggle. The face transfers heat and moisture to the air surrounding it. If the lens removes heat from the interior of the goggle then more heat needs to be added to the incoming air to avoid reaching the dew point on the surface of the lens.

Typically in skiing conditions the air outside the goggles is near or below the freezing point of water, thus containing little water. In drawing air into the interior of the goggle, the air will be heated by contact with the face, air filter, and lens, and the relative humidity near the wearer's face will drop below 100%. If the incoming air temperature were brought up to body temperature the air would have a relative humidity below 10%. This air absorbs moisture and flows out of the interior of the goggle.

Some of the features exemplary of, but not limited to, the present invention are summarized below:

The invention uses thermally conductive face contact materials in the face contact gasket to conduct heat from the cheek and nose body contact points to the air flowing into the face-lens volume while impeding the transfer of moisture from the body contact points to the face lens volume. This is a combination of a more thermally conductive face foam gasket with a moisture impermeable or reduced permeability barrier on the interior facing side. This gasket is then thermally coupled to surfaces of thermally conductive honeycomb air inlets, and or grooved or finned surfaces on the interior of the goggle frame. The face gasket can transfer heat internally by conduction, radiation, evaporation, condensation, convection and/or the like.

The face gasket includes, but is not limited to, the following features:

Open cell foam or cavities with interior sealed walls or channels in thermal contact with the face and the heat transfer surfaces. The body moisture will vaporize, diffuse, and condense on the adjacent goggle frame transferring heat to the frame or air heat transfer surfaces.

Thermally conductive metal, rubbers, and plastics incorporated in the face gasket.

Liquid-filled face gasket that transports heat by the high conductivity of the liquid or convection of the liquid.

Liquid and vapor-filled face gasket bladder that is a heat pipe to vaporize fluid at the body surface and condense the fluid at contact with the frame or heat transfer surfaces.

Radiant cavities in the gasket such that, by having high emissive interior surfaces, radiant heat is emitted and absorbed from the face contact to the frame of the goggle or the air heat transfer surfaces.

Air convection cells that transport heat from the body surface to the frame or air heat transfer surfaces. These could be channels in the face gasket that allow air to flow in the gasket between the face and the frame, but not into face lens region, to transport heat.

Form a face gasket, which moves condensed water on the interior surfaces under and near the gasket to the outer perimeter, by wicking, to be evaporated to the atmosphere.

The face gasket has the functions of moving water away from the surface of the skin outside the interior of the goggle and transferring heat to the goggle frame and heat transfer surfaces, while simultaneously sealing the goggle to the face to prevent snow from entering the interior of the goggle.

Create airflow inlet and outlet channels that have low impedance to flow while maximizing their heat transfer and snow blocking abilities to create a convective airflow regardless of outside air flow conditions.

This feature is essentially trying to optimize the natural convection within the goggle or a so-called "chimney effect". Air inside the face-lens volume is warmed and becomes buoyant. The air rises and exits out through outlet channels at the top of the goggle and is replaced by cold, outside air which is drawn into the face-lens volume through inlet channels at the bottom of the goggle. The lighter warm air removes moisture from the interior of the goggle as it rises, while the enclosure of the goggle maintains some snow blocking abilities.

One preferred embodiment uses a thermally conductive honeycomb, chevrons, or slotted inlets and outlets that are thermally connected to the face gasket. The effective diameter and length of the channels are sized to minimize air flow drag and maximize heat transfer while still blocking snow.

With a high enough air flow our research has shown that goggles in almost all cold weather conditions will remain clear. We have found, by testing commercially available goggles, that the typical snow filter foam has cell sizes and thicknesses that present a very high resistance to natural convection in goggles. The critical scaling parameter for air flow through these small air inlets (laminar flow) is air flow resistance per unit area, which is proportional to the length of the channels and inversely proportional to the square of the aperture size. In the present invention, the sizes of the inlet and outlet channels are such that natural convection within the goggle is achieved.

Form air flow channels that have a low flow impedance, block snow ingress, move fluids, such as but not limited to, liquid water, away from the face-lens volume and shield from air flow effects outside the goggle.

Our research has shown that heat transfer from the body to the air at the top of the goggle does not help significantly to clear the lens. On the other hand, it does help to avoid condensation in the top outlet channel and make a small contribution to the chimney effect thereby allowing moisture laden warm air vent out to the atmosphere. The other critical function of the top outlet channels are to prevent snow or liquid water from falling into the goggle. The lower air inlet channels have a larger effect on air flow and moisture removal. A typical problem will be condensation at the outlet which can drip back into the goggle. A "rain gutter" needs to be formed to move the condensed moisture away from the face-lens volume. Wicking or a hydrophilic channel to move water out of the face-lens volume is used in this invention. The lower air inlet is expected to have less snow impacting it and liquid water can exit.

Coatings on the air flow channels for optimum heat transfer, wetting and absorption properties.

The air flow channels can be coated with hydrophilic materials such as, but not limited to, solid polymer electrolytes that cause snow to melt and form a wetted film. The melted water may then be channeled out to a wicking system. The wetting coating prevents coalescence of water droplets and avoids condensed water blocking or dripping down into the goggle through the air channels. This helps make the channel surfaces sticky to snow and the liquid, thus making it easier to flow a film of water across them to the wicks. The flow channels may also act, to some degree, as moisture absorbing surfaces until they become saturated.

The coatings may have high emissivity (black) to also allow radiant heat to be transferred through the channel and the goggle and to avoid outside visible light being transmitted through the channel to the user. Absorption of ambient light also adds thermal energy to the air channels to help warm air and remove moisture.

These and further and other objects and features of the invention are apparent in the disclosure, which includes the above and ongoing written specification, with the claims and the drawings.

BRIEF DESCRIPTION OF THE DRAWINGS

FIGS. 1A, 1B, 1C, and 1D show a top, front face, and cutout side and enlarged side cutaway views of a goggle with an upper baffled vent.

FIGS. 2A, 2B, 2C, and 2D show a top, front face, and cutout side and enlarged side cutaway views of a goggle with an upper honeycombed baffle vent.

FIGS. 3A, 3B, 3C, and 3D show an interior face, bottom, and cutout side and enlarged side cutaway views of a goggle with a lower honeycombed baffled vent.

FIGS. 4A, 4B, 4C, 4D show a top, front face, and cutout side and enlarged side cutaway views of a goggle with an insertable upper baffled vent.

FIGS. 5A, 5B, 5C, 5D show a interior face, bottom, and cutout side and enlarged side cutaway views of a goggle with a lower baffled vent integrated into a face gasket.

DETAILED DESCRIPTION OF THE PREFERRED EMBODIMENTS

Figure 1D:
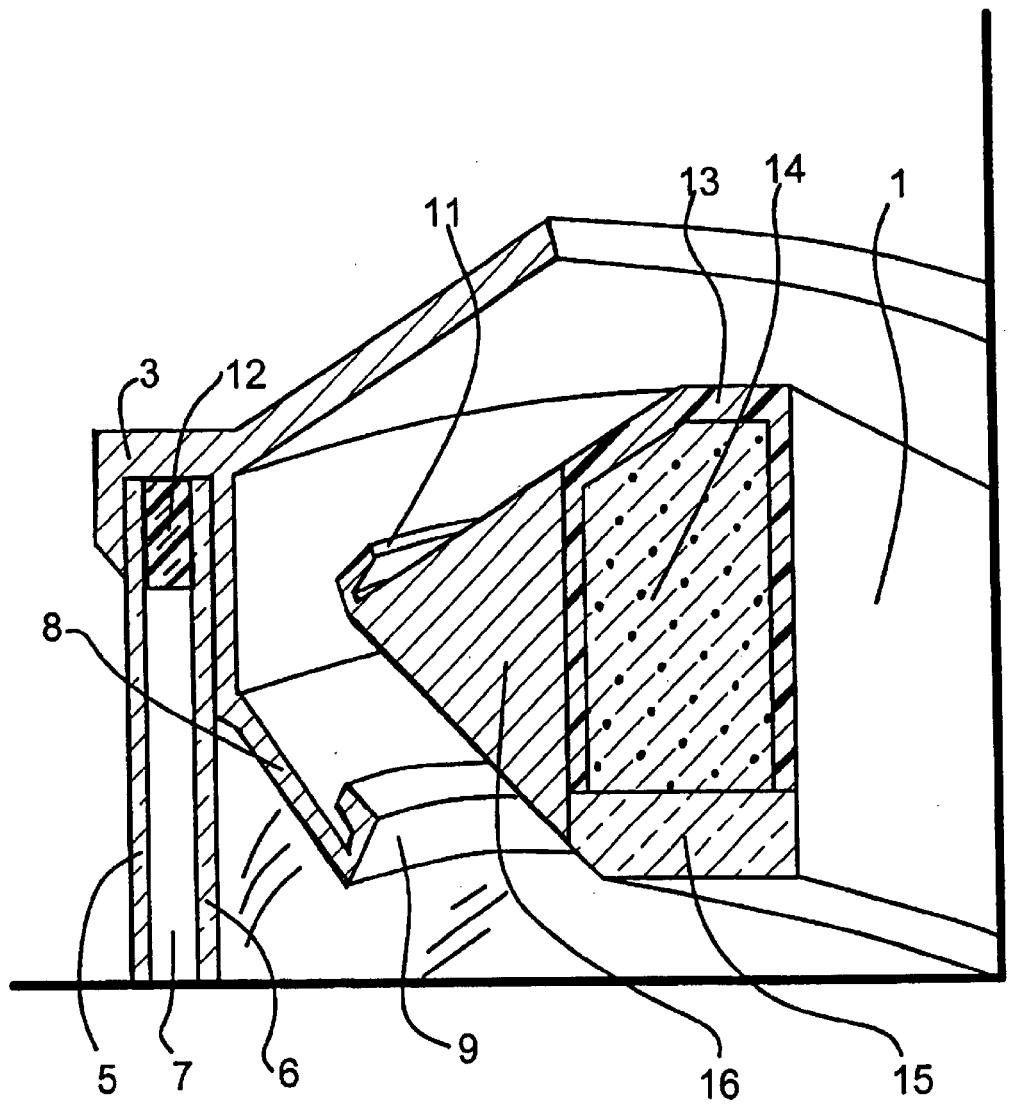

In FIGS. 1A, 1B, 1C, and 1D the top, front face, cutout side and enlarged side cutaway views of a goggle with an upper baffled vent are shown. In this design the upper baffle 2 is an air channel that runs along the top of the goggle. It is attached to the lens frame 3 of the goggle, which also holds the lens of the goggle 4. The goggle lens 4 shown in cross-section consists of an outer lens 5, a spacer foam 12 and an inner lens 6. The double lens 4 of the goggle achieves a low thermal conductivity by having an air gap 7 between the lenses and is often made more insulating by using low emissivity lens materials or coatings on the lenses. Both of these features reduce the heat transfer through the lens.

A face gasket 1 may be coupled to the frame by any known means such as, but not limited to, being glued (Acrylic Adhesive DP 8005, 3M Adhesives Division, St. Paul, Minn. 55144-1000) to the interior side of the frame 16 of the goggle. The upper baffle 2 is molded out of the urethane rubber frame 11 (Stevens Urethane, Nine Sullivan Road, Holyoke, Mass. 01040-2800) of the goggle to create a curved route from the inside of the face-lens volume to the upper exterior environment. The baffle consists of a lower baffle 8 that includes a water gutter 9. The water gutter 9 and lower baffle 8 extend across the top of the goggle so as to channel water from the melting of snow caught in the baffle and from condensed moisture in the interior of the goggle to the sides of the goggle and into face gasket absorbent wicks 13 (for example, COOL MAX® cloth, Intex Corporation, 1031 Summit Ave., Greensboro, N.C. 27405) on either side. Water can drip off the side ends of the gutter 9 or be absorbed by the head strap 17 to be evaporated. On the interior side 16 of the frame the other half of the airflow channel is formed. An upper water gutter 10 is molded into the polyurethane frame (Stevens Urethane, Nine Sullivan Road, Holyoke, Mass. 01040-2800).

The face gasket 1 is connected to, for example glued to, the second half of the baffle 2. This face gasket 1 is formed of open cell foam 14 covered with absorbent material, for example COOL MAX® cloth (Intex Corporation, 1031 Summit Ave., Greensboro, N.C. 27405) 13 or some other water-wicking, fabric or paper 14. The COOL MAX® cloth, 13 extends from under the frame 16, around the outer perimeter of the gasket 1, and under the face contact 18. A silicone rubber film 15 (for example, GE Silicones of General Electric Company, Waterford, N.Y., 12188), is applied to the surface of the face gasket in the interior of the goggle to block particulate matter and liquid and water vapor from entering the interior of the goggle.

In operation, water/sweat evaporates from the skin surface of the wearer or wick to the goggle frame 16 and to the outer perimeter of the face gasket 1. Heat conducts through the face gasket 15, 14, 13 to the goggle frame 16, 3 and transfers to the air flow in the upper baffle 2 and to the inner lens 6. We have found from experiments that heat transfer to the air leaving the interior of the goggle is less important than heat transfer to the air entering the interior of the goggle. The airflow in the upper baffle 2 is designed to have no straight line of flow. Snow, particulates, and rain will strike the sides of the upper baffle 2, lower baffle 8, and inside 16 of the frame and stick.

Figure 2D:
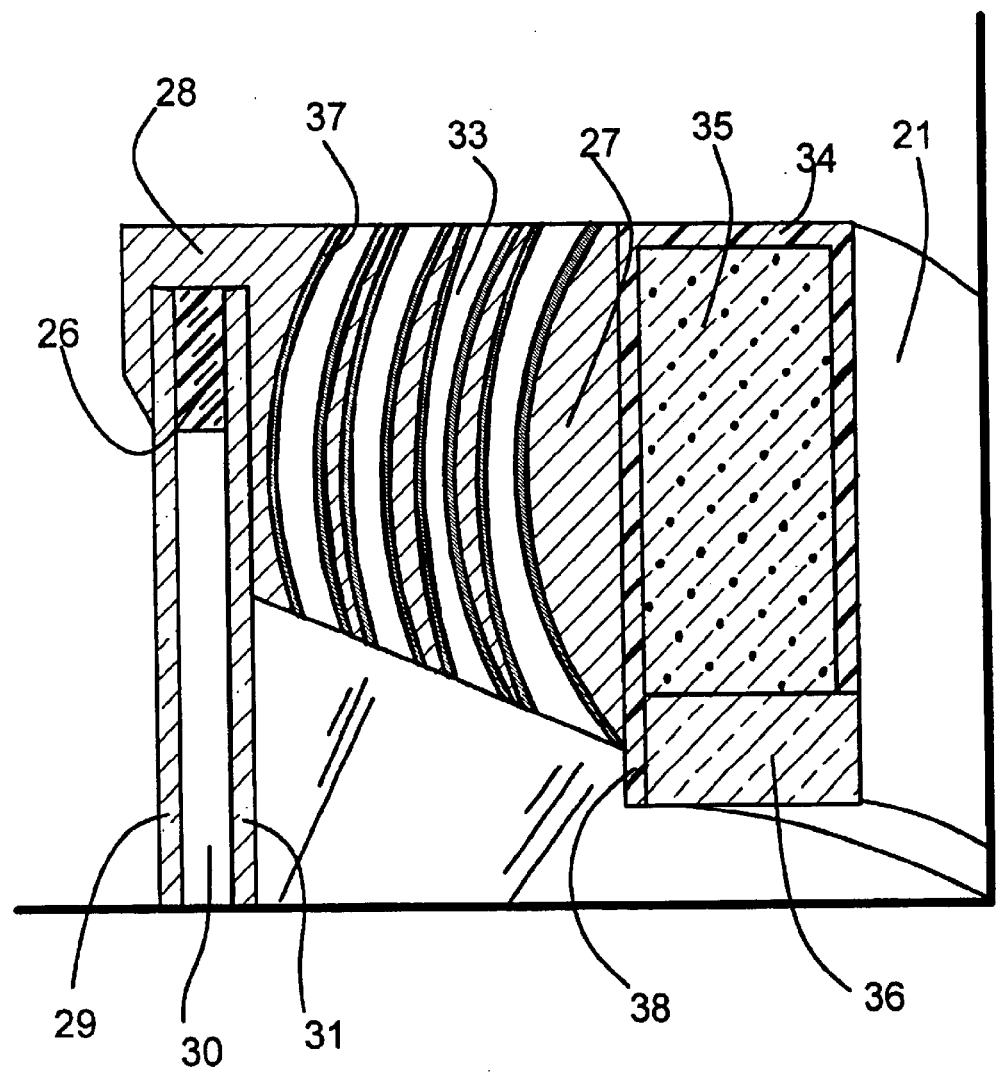

In FIGS. 2A, 2B, 2C, 2D the top, front face, cutout side, enlarged side cutaway views of a goggle with an upper honeycombed baffle vent are shown. The baffles of this system are formed such that the length, curvature and spacing result in no straight line of sight through the vent. In the top view the baffles 22 are shown interconnected in a honeycomb pattern of curved channels. The baffled vent can be formed by molding plastics, such as but not limited to, an ABS plastic (Regal Plastic, 5239 S. Rio Grande Ave., Littleton, Colo., 80120) or Urethane rubber (Stevens Urethane, Nine Sullivan Road, Holyoke, Mass. 01040-2800).

The baffles, upper baffle 32 and lower baffle 26, are molded into the goggle frame 23 and have openings at the top and bottom of the goggle. Only the top entrances are shown. A face gasket 21 is connected, for example glued (Acrylic Adhesive DP8005, 3M adhesives division, St. Paul, Minn. 55144-1000) to the interior side 27 of the frame. The material of the baffles 22, 26, 32 may be a single material or be a mixture of materials that give it a high thermal conductivity. In this design, for example, the baffles 32 are molded out of the plastic that forms the frame 28 of the goggle that also holds the goggle lens 24.

The goggle lens 24 shown in cross-section consists of an outer lens 29, a spacer foam 30, and an inner lens 31. The face gasket 21 is formed out of open cell foam 35 covered with absorbent material, for example COOL MAX® cloth 34 or other water wicking fabric or paper. The wicking cloth 34 contacts the face and extends around the gasket and under 27 the frame of the goggle. The wicking material extends up to the edge of the baffles 22 to catch liquid water condensed from the interior of the lens or melted from snow trapped by the baffles.

On the surfaces of the baffles are coatings 37 of a solid polymer electrolyte such as, but not limited to, NAFION® that wets when in contact with the snow. This wetting film keeps the water in the baffles from forming droplets and spreads the water film out over area of the baffles, to keep water from plugging the baffles. The electrolyte reduces the melting point temperature of the snow so it melts and wets at a lower temperature. Due to the pitch of the baffles 22 surface water can run down along the bottom of the baffle apertures 33 and walls 37 to reach the interior exposed wick edge 38. This allows the face gasket wicks 34 to wick water away from the face-lens volume out to the perimeter of the goggle. A silicone rubber film or any other thermally conductive, water-sealing film 36 is applied to the surface of the face gasket in the interior of the goggle to block liquid water and water vapor from entering the goggles.

Figure 3D:
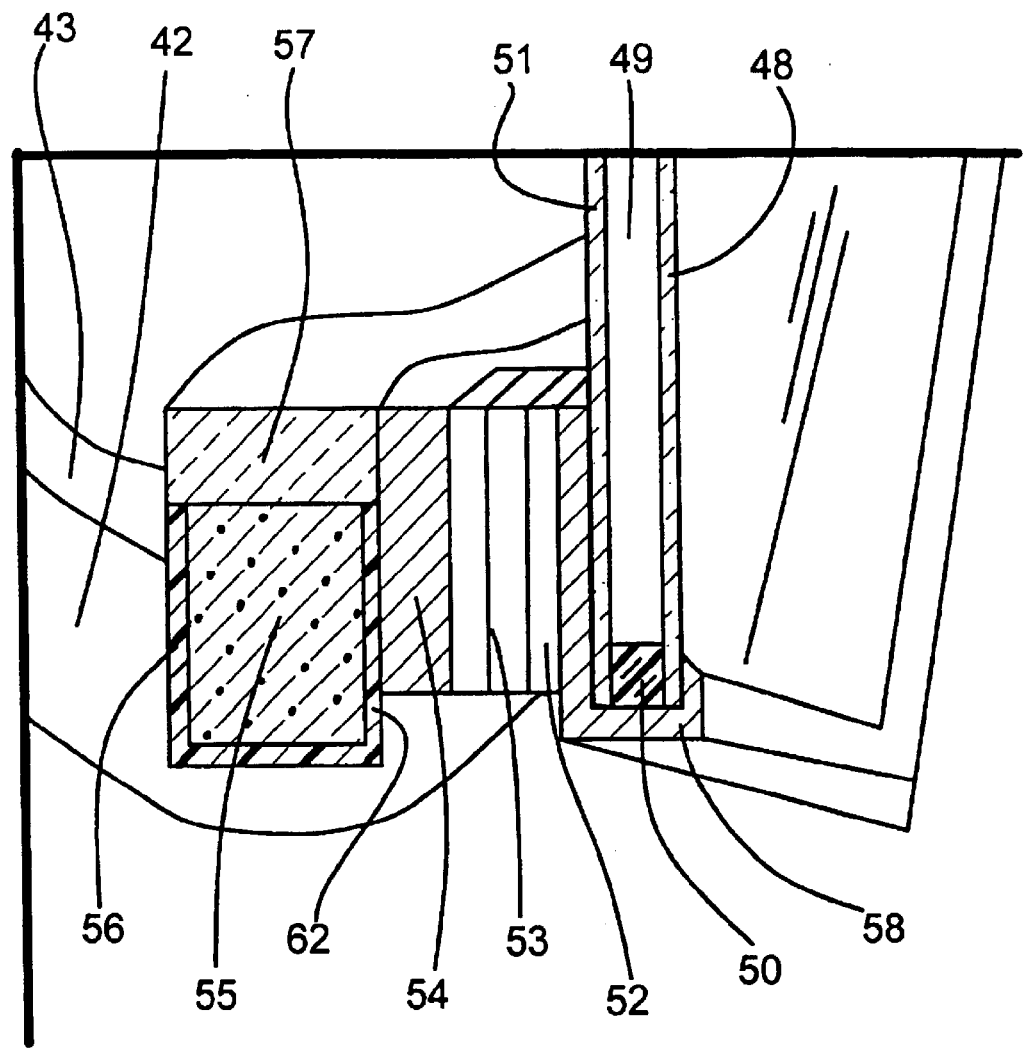

In FIGS. 3A, 3B, 3C, and 3D the interior face, bottom, cutout side and enlarged side cutaway views of a goggle with a lower honeycombed baffled vent are shown. In this design the inlets are thermally conductive air channels on either side of the nose portion. The air outlets can be either honeycombed or baffled vents 41 as shown in FIGS. 1A–1C and FIGS. 2A–2C. The inlets are honeycomb channels 59 molded out of plastic or rubber and molded into the rubber of the goggle frame 58.

Other thermally conductive materials that can be used include, but are not limited to, the following: magnesium metal, metal alloys such as TiNi, a thermally conductive plastic, metal-doped rubber or plastic, zirconium oxide powder-doped rubber, aluminum oxide powder-doped rubber, graphite-doped rubber or plastic, silicone rubber, natural rubber, polyaniline, polypyrrole, polypropylene, and polyurethane. The honeycomb 46, 59, 53, 52 is designed to have a high heat transfer to the incoming air while minimizing the drag on the incoming airflow and staying within the constraints of the goggle profile. Heat is transferred to the honeycomb 46, 59, 53, 52 and the goggle frame 54, 45, from the face gasket 42. Some heat is transferred through the honeycomb 59 and frame 58 to the goggle lens 44. Lower portions 60 are positioned over the nose of a user.

The goggle lens 44 coupled 43 to the gasket consists of an outer lens 48, a spacer foam 50, and an inner lens 51, with an air gap 49 between the inner and outer lens. The face gasket 42 is formed out of open cell foam 55 covered with absorbent material, such as COOL MAX® cloth 56 or some water-wicking fabric or paper. The wicking cloth 56 contacts the face and extends around the foam 55 and under 62 the frame 54 of the goggle. Water can evaporate from the surface of the user's skin and condense on the frame 54 of the face gasket-frame interface. The condensed water is wicked out to the perimeter of the face gasket 47, 56 and evaporates. On the interior of the face gasket is a thermally conductive and water-sealing film 57 to block water vapor from under the face gasket from going into the interior of the goggle.

Figure 4D:
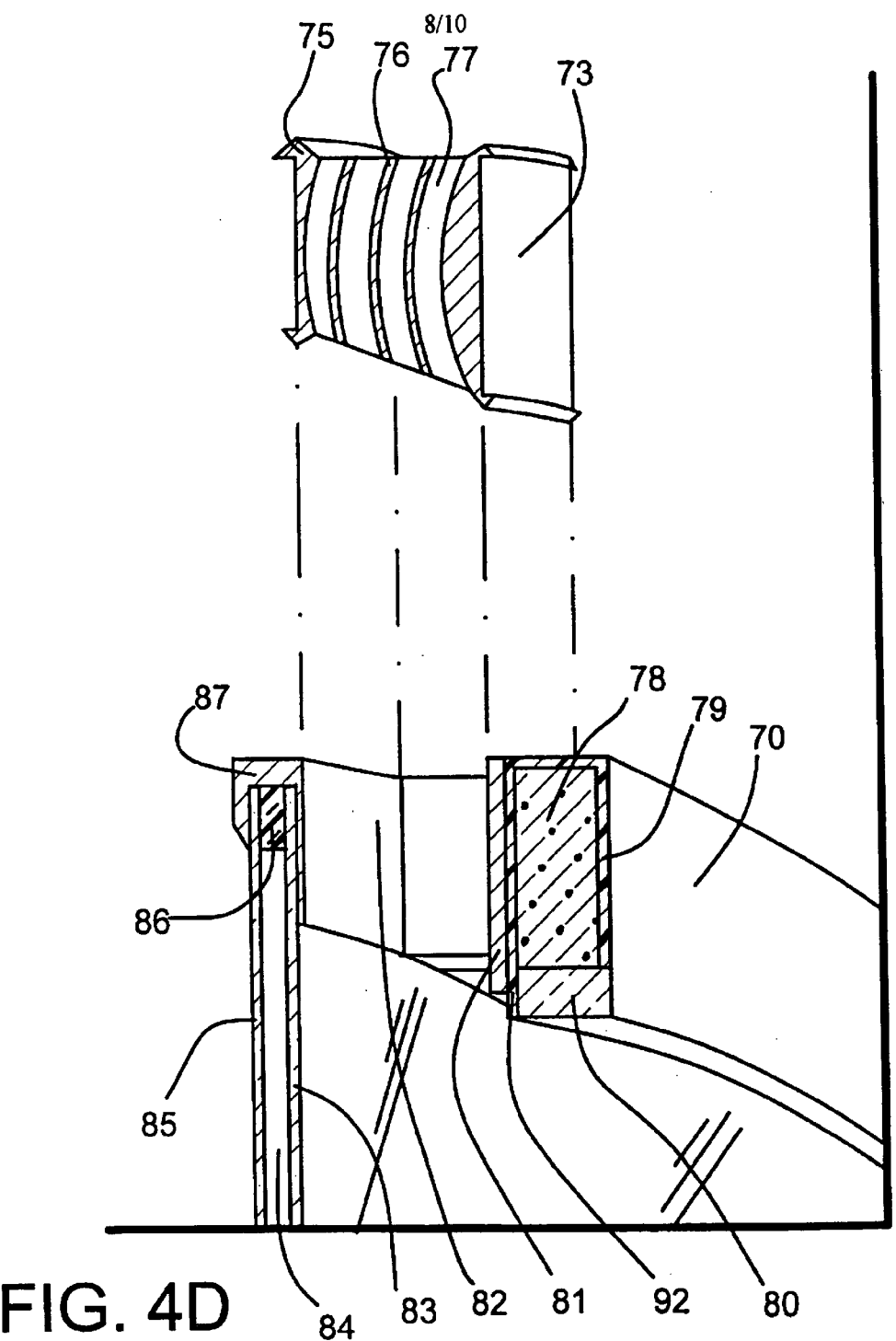

In FIGS. 4A, 4B, 4C and 4D the top, front face, and cutout side enlarged side cutaway views of a goggle with an insertable upper baffled vent are shown. In this design both the top and bottom of the vents can be inserted into the frame of the goggle. The baffle inserts 73 can be made out of a variety of thermally conductive materials including but not limited to aluminum, magnesium, TiNi, metal doped rubber or plastic, conductive plastics, graphite-doped rubber, silicone rubber, polypropylene, urethane. The insert is formed to fit and ratchet-lock 75 into apertures 82 in the goggle frame 81. Baffle inserts 73 can be formed to fit existing goggles in place of the foam-covered vents.

The face gasket 70, 71 is formed out of open cell foam 78 covered with COOL MAX® cloth 79 or other water-wicking fabric or paper. The wicking cloth 79 contacts the face and extends around the gasket and under the frame 81 of the goggle. The wicking material 92 extends up to the edge of the baffles 76 to catch liquid water condensed in the baffle channels 77 from the interior of the goggle or melted from snow trapped by the baffle 73. Due to the pitch of the baffle's lower surface 73, water can run down along the bottom of the baffle apertures 77 to reach the interior exposed wick 92 edge. This allows the wicking gasket 79 to wick water away from the interior of the goggle out to the perimeter of the face gasket 70.

On the interior of the face gasket 70 is a thermally conductive water-sealing film 80 to block water vapor from under the face gasket from entering into the interior of the goggle. The face gasket 70 can move heat by conduction, radiation, convection, and evaporation to the frame 81, 74 and the heat transfer baffle surfaces 76. Some heat is transferred through the baffle 73 and frame 72 webs to the goggle lens frame 74, 88, 90 and lens 89. The goggle lens 89 consists of an outer lens 85, a spacer 86, a spacer foam 87 and an inner lens 83, with an air gap 84 separating the inner and outer lenses.

Figure 5D:
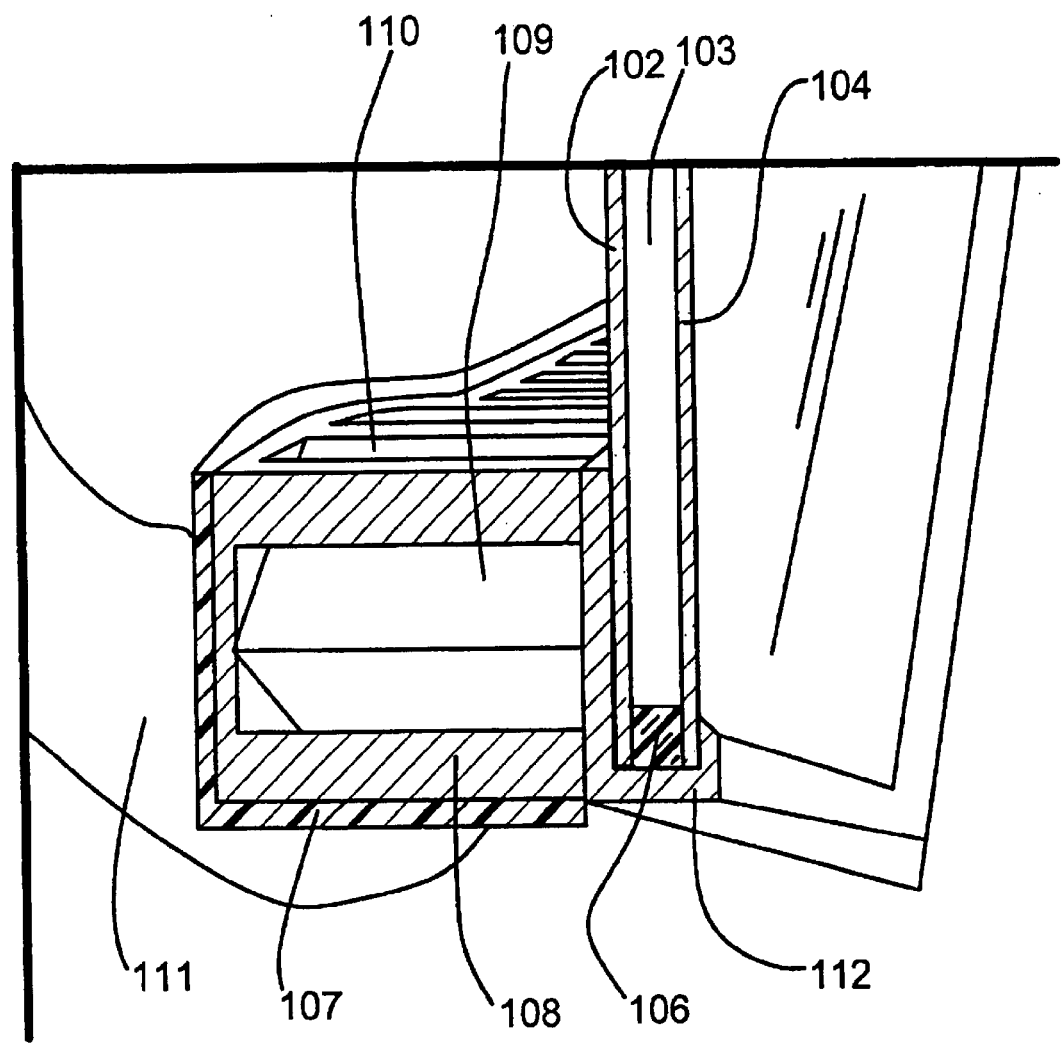

In FIGS. 5A, 5B, 5C, 5D the bottom, interior face and cutout side and enlarged side cutaway views of a goggle with a lower baffled vent integrated into the face gasket are shown. In this design the baffle vents are thermally conductive air channels formed in the face gasket. The baffle vents 113, 115 are formed in the face gasket 112 out of open cell foams, closed cell foam, rubbers, or plastics. The air channels 115, 113 are defined by chevroned walls 116 in the face gasket on frame 96.

The face gasket 98, 111, 112 serves several purposes: It seals the goggle from snow ingress, vents the goggle, transfers heat to the inlet air and wicks water away from the skin. The baffled vents 108 can be laminated or molded into the face gasket 98, 111, 112, 114. They are designed by choosing the aperture size 113, 110 and minimum channel 109 path that blocks snow and has a high heat transfer to incoming air, while minimizing the drag on the incoming air and staying within the constraints of the goggle profile.

Body heat is transferred through the COOL MAX® cloth 107, 97 to the face gasket 98 from face contact by conduction, radiation, evaporation and condensation. Some heat is transferred through the face gasket 98 to the goggle frame 105, 100 and lens 101.

The goggle lens 101, 99 consists of an outer lens 104, an inner lens 102, and a spacer foam 106. The spacer foam 106 creates an air gap 103 between the inner and outer lens. The face gasket is formed out of open cell foam covered with COOL MAX® cloth 107, 97 or other water-wicking fabric or paper. The wicking cloth 107, 97 contacts the face and extends around to the outer surface of the face gasket. Water, moisture, sweat can wick from the surface of the user's skin and evaporate on the outer perimeter of the face gasket 107. On the interior of the face gasket the heat transfer channels 109 are sealed with a thermally conductive water-sealing film to block water vapor from entering the air inlet flow and to use the heat of condensation to add heat to the inlet air without moisture.

The invention has been described in detail with particular reference to the preferred embodiments thereof. Those skilled in the art will recognize that many modifications, variations, substitutions and alterations are possible without departing from the scope of the invention.

While the invention has been described with reference to specific embodiments, modifications and variations of the invention may be constructed without departing from the scope of the invention, which is defined in the following claims.

We claim:

1. A goggle comprising a frame, a lens on the frame, a gasket in contact with a face of a user, a thermal transport conduit communicating with the gasket, and a heat transfer system formed by the thermal transport conduit for transporting heat away from the face of the user, further comprising at least one inlet vent communicating with the frame and at least one outlet vent communicating with the frame, wherein the frame comprises fluid absorbing material, and wherein the fluid absorbing material is a coating on the inlet vent.

2. The goggle of claim 1, wherein the heat transfer system is selected from the group consisting of conduction, radiation, convection, evaporation-condensation, and combinations thereof.

3. The goggle of claim 1, wherein the heat transfer system transfers heat to air or to the lens and minimizes transport of water vapor to an interior volume of the goggle.

4. The goggle of claim 1, wherein the gasket is of thermally conductive material.

5. The goggle of claim 4, wherein the thermally conductive material is selected from the group consisting of metals, metal alloys, thermally conductive plastic, metal-doped rubber, metal-doped plastic, graphite-doped rubber, graphite-doped plastic, silicone rubber, natural rubber, polypropylene, polyurethane, air cavity with high emissivity walls, liquid filled bladder, open cell foam partially filled with water, and combinations thereof.

6. The goggle of claim 4, wherein the thermally conductive material is selected from the group consisting of aluminum, magnesium, TiNi, polyaniline and polypyrrole.

7. The goggle of claim 1, wherein the fluid absorbing material is a coating on the outlet vent.

8. The goggle of claim 1, further comprising a wick in the frame for wicking fluids from an interior of the goggle and for minimizing fluid entry into the interior of the goggle.

9. The goggle of claim 1, further comprising an inlet flow channel, an outlet flow channel, and baffles on the inlet and the outlet flow channels, wherein the flow channels allow air to flow through into an inner space between the lens of the goggle and the face with minimum drag.

10. The goggle of claim 9, wherein the inlet channel filters out and excludes snow, dust, and particulate matter from the inner space.

11. The goggle of claim 9, wherein the outlet channel filters out and excludes snow, dust and particulate matter from the inner space.

12. The goggle of claim 9, further comprising couplings for thermally coupling the flow channels to the gasket of the goggle.

13. The goggle of claim 9, further comprising wicking material in the gasket, wherein the flow channels channel fluids to the wicking material from and away from the inner space of the goggle.

14. The goggle of claim 9 further comprising insertable modules comprising the flow channels and the baffles, wherein the modules are removably insertable into the frame of the goggle.

15. The goggle of claim 9, wherein the flow channels and the baffles are integral with the gasket of the goggle.

16. The goggle of claim 1, further comprising a fluidproof sealing film on an interior of the face gasket.

17. An eyewear device comprising a frame, lenses on the frame, a gasket coupled to the frame contacting a user's face, thermally conductive fluid-absorbing contact channels on the frame for conducting heat from the face to air flowing into the face-lens volume while impeding transfer of moisture to the face-lens volume.

18. The device of claim 17, wherein the thermally conductive material is incorporated in the channels.

19. The device of claim 18, wherein the thermally conductive fluid-absorbing material is selected from a group consisting of foam, metal, rubber, plastic, and combinations thereof.

20. The device of claim 18, wherein the thermally conductive material incorporated in the channels forms a moisture impermeable barrier or a reduced moisture permeability barrier on an interior facing side of the frame.

21. The device of claim 18, wherein the channels are vents disposed adjacent to the frame forming heat transfer surfaces for thermally conducting heat away from the face.

22. The device of claim 21, further comprising couplings for thermally coupling the gasket to surfaces of the vents.

23. The device of claim 22, wherein the vents are selected from a group consisting of thermally conductive honeycomb air inlets, grooved surfaces, finned surfaces, baffles, chevrons, slotted inlets and outlets, and combinations thereof.

24. The device of claim 22, wherein the vents are thermally conductive for transferring heat from the face by a method selected from a group consisting of conduction, radiation, evaporation, condensation, convection, and combinations thereof.

25. The device of claim 21, wherein the vents are provided from a group consisting of open or closed cell foam, cavities with interior sealed walls, channels, honeycombs, baffles, and combinations thereof.

26. The device of claim 21, wherein the vents absorb moisture vaporizing from the face and condense the moisture on the frame by transferring heat to the frame or the heat transfer surfaces.

27. The device of claim 21, wherein the vents are liquid filled bladders for conducting heat away from the face by conductivity or convection of the liquid.

28. The device of claim 21, wherein the vents are fluid and vapor filled bladders for vaporizing moisture from the face and condensing the moisture contacting the frame or the heat transfer surfaces.

29. The device of claim 21, wherein the vents are radiant cavities having high emissive interior surfaces for emitting radiant heat, absorbing moisture from the face and transferring to the frame or the heat transfer surfaces.

30. The device of claim 21, wherein the vents are air convection cells for transporting heat from the face to the frame or air heat transfer surfaces.

31. The device of claim 21, wherein the vents allow air to flow in between the face and the frame but not onto the lenses.

32. The device of claim 21, further comprising a wick on the gasket for wicking and moving condensed fluids on interior surfaces under and near the gasket to an outer perimeter for evaporating into ambient atmosphere.

33. The device of claim 21, wherein the gasket moves moisture away from the face, transfers heat to the frame and heat transfer surfaces, while simultaneously sealing the frame to the face to prevent particles from entering an interior of the eyewear.

34. The device of claim 21, wherein the vents form inlet and outlet air flow channels for having low impedance to flow while maximizing heat transfer and snow blocking abilities and creating convective air flow regardless of outside air flow conditions.

35. The device of claim 34, wherein the heat transfer surfaces enable warm air inside the face-lens volume to become buoyant, rise and exit out through the outlet channels for being replaced by cold, outside air drawn into the face-lens volume through the inlet channels, and wherein the rising warm air removes moisture from an interior of the eyewear.

36. The device of claim 34, wherein the inlet and the outlet channels have a low flow impedance, block snow ingress, move fluids away from the face-lens volume and shield the face from outside air flow effects.

37. The device of claim 34, wherein the inlet channels are on a bottom of the frame for facilitating air flow into an interior of the eyewear, and wherein the outlet channels are on a top of the frame for preventing snow or fluids from entering the eyewear.

38. The device of claim 37, further comprising a deflector for deflecting condensed moisture away from the face-lens volume and preventing condensed moisture from dripping back into the eyewear.

39. The device of claim 37, further comprising a hydrophilic channel for moving moisture away from the face-lens volume.

40. The device of claim 39, wherein the hydrophilic channel comprises a wick for removing the moisture.

41. The device of claim 34, further comprising coatings for optimum heat transfer, wetting and absorption, properties.

42. The device of claim 41, wherein the coatings are incorporated in the gasket and the channels.

43. The device of claim 42, wherein the coatings are of hydrophilic materials.

44. The device of claim 43, wherein the materials are solid polymer electrolytes for melting snow and for forming a wetted film thereby preventing coalescence of moisture and preventing condensed moisture from blocking or dripping down into an interior through the channels.

45. The device of claim 44, further comprising wicks for wicking moisture away from the interior of the eyewear.

46. The device of claim 42, wherein the coatings have high emissivity for allowing radiant heat to be transferred out through the channels and simultaneously preventing outside visible light from being transmitted through the channels to the user.

47. The device of claim 46, wherein the coatings absorb ambient light for adding thermal energy to the channels, warming air in an interior of the eyewear and removing moisture.

48. The device of claim 34, wherein the inlet channels are removably insertable in the eyewear.

49. The device of claim 34, wherein the outlet channels are removably insertable in the eyewear.

50. The device of claim 21, wherein the lenses further comprise an outer lens, a spacer, and an inner lens enabling low thermal conductivity.

51. The device of claim 50, wherein the lenses comprise insulating low emissivity materials or coatings on the lenses and the spacer is an air gap between the outer and the inner lenses for reducing heat transfer through the lenses.

52. The device of claim 21, wherein the vents comprise baffles having an upper baffle forming a curved route from an inside of the face-lens volume to an upper exterior environment, and a lower baffle comprising a gutter extending across a top of the gasket for channeling fluids from the baffle and condensed moisture in the inside to sides of the eyewear.

53. The device of claim 52, further comprising wicks on sides of the gasket for receiving the moisture channeled to the sides of the gutter.

54. The device of claim 53, wherein the wicks are of moisture-wicking material.

55. The device of claim 53, wherein the wicks are disposed under the frame, around an outer perimeter of the gasket, and under face contact areas of the gasket.

56. The device of claim 55, further comprising a fluid repellant thermally conductive film on inner surfaces of the gasket for blocking fluids and vapors from entering an interior of the eyewear.

57. The device of claim 52, wherein the lower baffle comprises thermally conductive channels and is positionable on a nose of the user.

58. The device of claim 52, wherein the thermally conductive material is selected from a group consisting of plastic, rubber, magnesium metal, metal alloys, TiNi, thermally conductive plastic, metal-doped rubber or plastic, zirconium oxide powder-doped rubber, aluminum oxide powder-doped rubber, graphite-doped rubber or plastic, silicone rubber, natural rubber, polyaniline, polypyrrole, polypropylene, polyurethane, and combinations thereof.

59. The device of claim 52, wherein the upper baffle is removably insertable in the eyewear.

60. The device of claim 51, wherein the lower baffle is removably insertable in the eyewear.

61. The device of claim 52, wherein the baffles are of thermally conductive materials selected from a group consisting of aluminum, magnesium, TiNi, metal doped rubber or rubber, polyproplene, urethane, and combinations thereof.

62. The device of claim 21, wherein the vents are removably insertable in the eyewear.

63. The device of claim 21, wherein the vents are laminated or molded into the gasket.

64. The device of claim 21, wherein the vents have aperture sizes and channel paths conducive to blocking snow and transferring heat while minimizing drag on incoming air.

* * * * *